US006413934B1

(12) United States Patent
Stayton et al.

(10) Patent No.: US 6,413,934 B1
(45) Date of Patent: Jul. 2, 2002

(54) STREPTAVIDIN MUTANTS HAVING SECONDARY FUNCTIONAL DOMAINS

(75) Inventors: Patrick S. Stayton; Todd C. McDevitt; Kjell E. Nelson, all of Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/382,276

(22) Filed: Aug. 25, 1999

Related U.S. Application Data

(60) Provisional application No. 60/097,816, filed on Aug. 25, 1998.

(51) Int. Cl.$^7$ .............................................. C07K 14/00

(52) U.S. Cl. ...................................... 514/12; 530/350

(58) Field of Search ................. 514/11, 12; 424/194.1; 530/402, 327, 350; 435/69.1, 69.7

(56) References Cited

U.S. PATENT DOCUMENTS

| 4,458,066 A | | 7/1984 | Caruthers et al. | |
| 4,839,293 A | * | 6/1989 | Cantor et al. | ................ 435/320 |
| 5,328,985 A | | 7/1994 | Sano et al. | |
| 5,443,955 A | | 8/1995 | Cornell et al. | |
| 5,492,890 A | * | 2/1996 | Ginsberg et al. | ............... 514/12 |

FOREIGN PATENT DOCUMENTS

WO    WO 96/24606    8/1996

OTHER PUBLICATIONS

McDevitt, et al., "Constrained cell recognition peptides engineered into streptavidin," *Chem. Abs.* 131:57810 (1999).
Katz & Cass, "In crystals of complexes of Streptavidin with peptide ligands containing the HPQ sequence the $pK_a$ of the peptide histidine is less than 3.0," *J Biol Chem* 272(20):13220–28 (1997).
Rezania & Healy, "Biomimetic peptide surfaces that regulate adhesion, spreading, cytoskeletal organization, mineralization of the matrix deposited by osteoblast–like cells," *Biotechnol Prog* 15(1):19–32 (1999).
Yamada, et al., "Structure of a conformationally contrained Arg–Gly–Asp sequence inserted into human lysozyme," *J Biol Chem* 270(11):5687–90 (1995).
Alon, et al., "Cell–adhesive properties of streptavidin are mediated by the exposure of an RGD–like RYD site," *Eur J Cell Biol.* 58(2):271–9 (1992).
Alon, et al., "Streptavidin blocks immune reactions mediated by fibronectin–VLA–5 recognition through an Arg–Gly–Asp mimicking site," *Eur J Immunol.* 23(4):893–8 (1993).
Alon, et al., "Streptavidin contains an RYD sequence which mimics the RGD receptor domain of fibronectin," *Biochem Biophys Res Commun.* 170(3):1236–41 (1990).

Argarana et al., "Molecule Cloning and Nucleotide Sequence of the Streptavidin Gene," *Nucl. Acids. Res.* 14:1871–1882 (1986).
Barbas, et al., "High–affinity self–reactive human antibodies by design and selection: targeting the integrin ligand binding site," *Proc Natl Acad Sci U S A.* 90(21):10003–7 (1993).
Beaucage, et al., "Deoxynucleoside phosphoramidites–a new class of key intermediates for deoxypolynucleotide synthesis," *Tetra. Lett.* 22:1859–1862 (1981).
Berenson, et al., "Transplantation of stem cells enriched by immunoadsorption," *Prog Clin Biol Res.* 377:449–59 (1992).
Brown, et al., "Chemical synthesis and cloning of a tyrosine tRNA gene," *Meth. Enzymol.* 68:109–151 (1979).
Chilkoti, et al., "Site–directed mutagenesis studies of the high–affinity streptavidin–biotin complex: contributions of tryptophan residues 79, 108, and 120,". *Proc Natl Acad Sci USA* 92:1754–1758 (1995).
D'Souza, et al., "Arginyl–glycyl–aspartic acid (RGD): a cell adhesion motif," *Trends Biochem Sci.* 16(7):246–50 (1991).
Green, "Avidin," *Adv Protein Chem.* 29:85–133 (1975).
Gross & Meienhofer, The Peptides; Analysis, Synthesis, Biology vol. 2. Special Methods in Peptide Synthesis, Part A, Academic Press:London, 1980.
Hashino, et al., "Engineering of artificial cell adhesion proteins by grafting the Arg–Gly–Asp cell adhesive signal to a calpastatin segment," *J Biochem (Tokyo).* 112(4):547–51 (1992).
Maeda, et al., "A novel cell adhesive protein engineered by insertion of the Arg–Gly–Asp Ser tetrapeptide," *J Biol Chem.* 264(26):15165–8 (1989).
Main, et al., "The three–dimensional structure of the tenth type III module of fibronectin: an insight into RGD–mediated interactions," *Cell.* 71(4):671–8 (1992).
Merrifield, et al., "Solid phase peptide synthesis. I. The syntesis of a tetrapeptide," *J. Am. Chem. Soc.* 85:2149–2156 (1963).

(List continued on next page.)

*Primary Examiner*—Karen Cochrane Carlson
(74) *Attorney, Agent, or Firm*—Holland & Knight LLP

(57) ABSTRACT

Streptavidin molecules are disclosed that contain a secondary functional domain. In preferred embodiments, the secondary domain is a cell adhesion peptide incorporated in the streptavidin amino acid sequence at a site not interfering with biotin binding. In a preferred embodiment, the cell adhesion peptide is arginine-glycine-aspartate (Arg-Gly-Asp) (RGD). The peptide is preferably placed on an exposed loop of the streptavidin molecule, such as within the loop defined by residues 63 to 69. The mutant streptavidin molecule can have other characteristics such as reduced biotin binding due to a modification of an amino acid at the biotin binding site. Preferred uses for the disclosed streptavidin molecules are as adaptors to bring, via a streptavidin/biotin interaction, the secondary functional domain into proximity with a cell or molecule to be affected and as a coating for substrates such as vascular devices or prostheses.

12 Claims, 4 Drawing Sheets

OTHER PUBLICATIONS

Meyer, et al., "Streptavidin–Biotin Immunotoxins: A New Approach to Purging Bone Marrow," *Exp. Hematol.* 19:710–713 (1991).

Narang, et al., "Improved phosphotriester method for the synthesis of gene fragments," *Meth. Enzymol.* 68:90–98 (1979).

Pierschbacher & Ruoslahti, "Cell attachment activity of fibronectin can be duplicated by small synthetic fragments of the molecule," *Nature.* 309(5963):30–3 (1984).

Pierschbacher, et al. "Influence of stereochemistry of the sequence Arg–Gly–Asp–Xaa on binding specificity in cell adhesion," *J. Biol. Chem.* 262(36):17294–8 (1987).

Rossi, et al., "Engineered idiotypes. Immunochemical analysis of antigenized antibodies expressing a conformationally constrained Arg–Gly–Asp motif," *Mol Immunol.* 32(5):341–6 (1995).

Sano & Cantor, "Expression Vectors for Streptavidin–Containing Chimeric Proteins," *Biochem. Biophys. Res. Commun.* 176:571–577 (1991).

Smith, et al., "Protein loop grafting to construct a variant of tissue–type plasminogen activator that binds platelet integrin alpha llb beta 3," *J Biol Chem.* 270(51):30486–90 (1995).

Stewart, et al., Solid Phase Pepetide Synthesis, 2nd ed. Pierce Chem. Co.: Rockford, Ill., 1984.

Weber, et al., "Structural origins of high–affinity biotin binding to streptavidin," *Science* 243–85–88 (1989).

Wilchek & Bayer, "Introduction to Avidin–Biotin Technology," *Meths. Enzymol.* 184:5–45 (1990).

Yamada & Kennedy, "Dualistic nature of adhesive protein function: fibronectin and its biologically active peptide fragments can autoinhibit fibronectin function," *J Cell Biol.* 99(1Pt 1):29–36 (1984).

Yamada, et al., "Structure of a conformationally constrained Arg–Gly–Asp sequence inserted into human lysozyme," *J Biol Chem.* 270(11):5687–90 (1995).

* cited by examiner

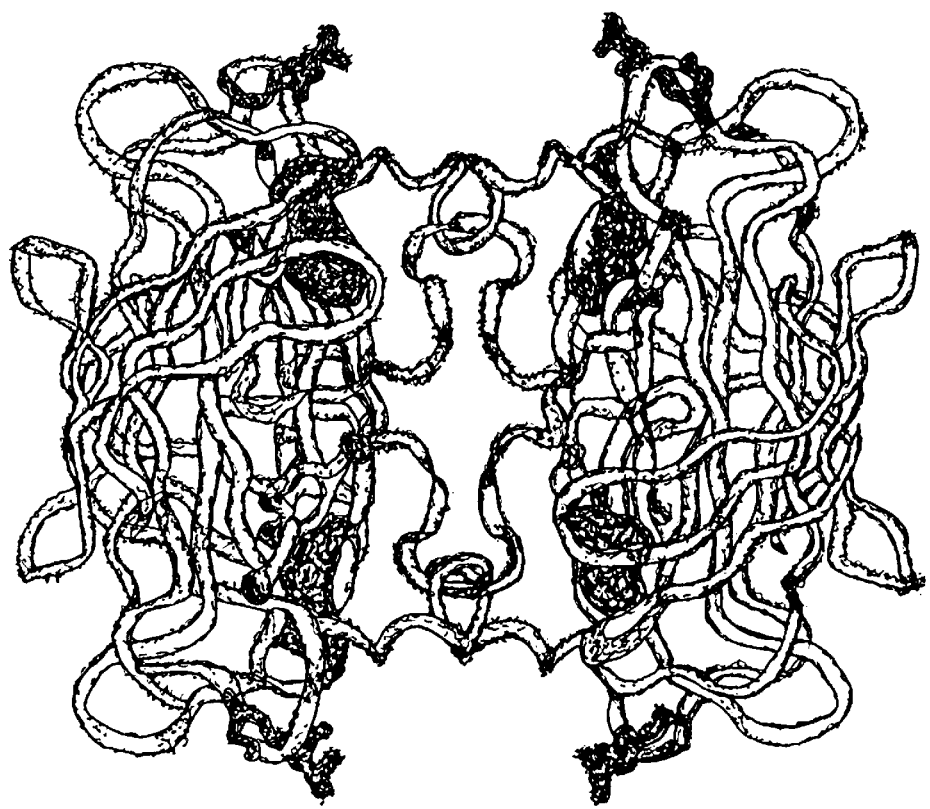
FIG. 1
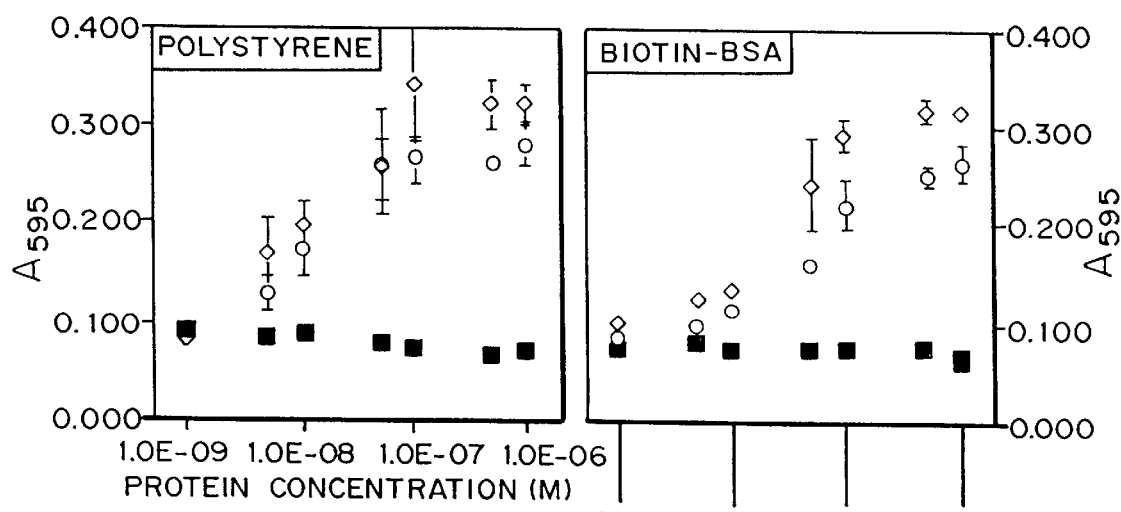
FIG. 2A
FIG. 2B

STREPTAVIDIN MUTANTS HAVING SECONDARY FUNCTIONAL DOMAINS

CROSS-REFERENCE TO RELATED APPLICATIONS

This application claims benefit of U.S. Provisional Application No. 60/097,816, filed Aug. 25, 1998. Provisional Application Serial No. 60/097,816, filed Aug. 25, 1998, is hereby incorporated herein by reference.

STATEMENT REGARDING FEDERALLY SPONSORED RESEARCH

The Federal government has certain rights in the invention by virtue of NIH grant DK49655 to Dr. Patrick Stayton.

BACKGROUND OF THE INVENTION

The present invention is directed to streptavidin molecules having secondary functional domains such as a cell adhesion domain.

Streptavidin, a protein produced by *Streptomyces avidinii*, forms a very strong and specific non-covalent complex with the water soluble vitamin biotin. Streptavidin is a tetrameric protein that binds biotin with an affinity that is among the highest displayed for non-covalent interactions between a ligand and protein, with an association constant (Ka) estimated to be in the range of $10^{13} M^{-1}$ to $10^{15} M^{-1}$. This binding affinity is strong enough to be essentially irreversible under normal physiological solution conditions, and provides the basis for streptavidin and biotin's usefulness in a wide variety of clinical and industrial applications. See, Green, *Adv. Prot. Chem.* 29:85–143 (1975).

Both streptavidin and the homologous protein avidin, which shares its high affinity for biotin, have been studied as paradigms of strong ligand-protein interactions. The X-ray crystal structures of streptavidin and avidin, both in their apo and holo forms, have been described. The sequences of both have also been reported, as have the construction of several streptavidin fusion proteins (Sano and Cantor, *Biochem. Biophys. Res. Commun.* 176:571–577 (1991); U.S. Pat. No. 4,839,293).

In addition to the extremely high binding affinity, the usefulness of streptavidin also arises from the unique architectural properties of the protein. Streptavidin is a tetramer of four identical subunits, with each subunit contributing a binding site for biotin. Because the tetramer has approximate two-fold symmetry, the binding sites are positioned in pairs on opposite sides of the molecule, making the protein an efficient molecular adaptor. This structural feature, along with the high affinity of streptavidin for biotin, has made the protein an important component in many technologies.

Streptavidin is a key components in four technological areas of great significance: 1) bioseparations/cell sorting; 2) imaging; 3) drug delivery; and 4) diagnostics (Wilchek and Bayer, in *Meths. Enzymol.* 184:5–45 (1990)). In the separations area, this protein has been used extensively in important cell sorting applications, where, for example, it is used to remove contaminating cells from hematopoietic stem cells prior to marrow transplantation. Berenson et al., *Prog. Clin. Bol. Res.* 377:449–459 (1992). Streptavidin has found similar wide use in cancer diagnostics, where it is used in both research and clinical settings to test for the presence of various tumor specific biomarkers.

The imaging and drug delivery applications of streptavidin and biotin arise from the capability for simultaneous targeting and delivery of imaging agents or therapeutics to tumor cells. There is particularly significant emerging interest in the use of streptavidin for targeted delivery of imaging agents and therapeutics in vivo. Streptavidin has been used to deliver drugs, toxins and imaging agents to targeted cells both in vitro and in vivo. See, for example, Meyer et al., *Exp. Hematol.* 19:710–713 (1991). In these systems, streptavidin plays the crucial role of molecular adaptor between an antibody that serves as the targeting component, and a biotinylated therapeutic or imaging agent. With some strategies, cells are pre-targeted with the antibody-streptavidin conjugate, with subsequent delivery of the biotinylated agent. In other applications, a biotinylated antibody is first used to pre-target cells, with subsequent delivery of the streptavidin-biotinylated agent conjugate. A three-step delivery is also possible, using biotinylated antibody followed by streptavidin and then the biotinylated agent.

It would be advantageous to have a streptavidin molecule that contains a secondary functional domain so that biotin binding is retained but the streptavidin molecule also has another function. For example, it would be advantageous to have a streptavidin molecule that binds to a cell so that, for example, molecules can be selectively delivered to that cell. It would be advantageous to have streptavidin that selectively binds to a particular cell type or to a particular protein so that selective purification can be performed.

BRIEF SUMMARY OF THE INVENTION

Streptavidin molecules are disclosed that contain a secondary functional domain. In preferred embodiments, the secondary domain is a cell adhesion peptide incorporated in the streptavidin amino acid sequence at a site not interfering with biotin binding. In a preferred embodiment, the cell adhesion peptide is arginine-glycine-aspartate (Arg-Gly-Asp) (RGD). The peptide is preferably placed on an exposed loop of the streptavidin molecule, such as within the loop defined by residues 63 to 69. The mutant streptavidin molecule can have other characteristics such as reduced biotin binding due to a modification of an amino acid at the biotin binding site. Preferred uses for the disclosed streptavidin molecules are as adaptors to bring, via a streptavidin/biotin interaction, the secondary functional domain into proximity with a cell or molecule to be affected and as a coating for substrates such as vascular devices or prostheses.

BRIEF DESCRIPTION OF THE DRAWINGS

FIG. 1 is a schematic model of an example of a mutant streptavidin molecule as described herein and its orientation on a biotinylated surface. Black side-chains represent the RGD residues and biotin is represented as the gray ball-and-stick atoms. The model does not attempt to predict the precise structure of the loop into which RGD is inserted, but simply depicts the spatial relationships of biotin and the RGD mutations.

FIGS. 2A and 2B are graphs of absorbance at 595 nm (representing adhered cells) versus concentration of streptavidin having incorporated therein RGD with flanking amino acids as in fibronectin (FN-SA) and streptavidin having incorporated therein RGD with flanking amino acids as in osteopontin (OSTP-SA). FN-SA (diamonds) and OSTP-SA (circles) were coated on either polystyrene (FIG. 2A) or biotin-BSA adsorbed onto polystyrene (FIG. 2B) and compared to adhesion of wild type streptavidin (black squares).

FIG. 4A is a graph of absorbance at 595 nm (representing adhered cells) versus concentration of FN-SA and OSTP-SA. FIG. 4B is a graph of absorbance at 595 nm (representing adhered cells) versus concentration of RGD peptides used as a competitor of cell adherence to FN-SA and OSTP-SA. The streptavidin coating concentration in the experiment of FIG. 4B was kept constant at 200 μM. Error bars indicate ±standard deviation (n=3).

FIG. 5A is a graph of absorbance at 595 nm (representing adhered cells) using SAMs coated with FN-SA, OSTP-SA, and wild type streptavidin. FIG. 5B is a bar graph of absorbance at 595 nm (representing adhered cells) to FN-SA (mottled-bars) or OSTP-SA (horizontal bars) following preincubation of the cell suspension in the presence of 10 μg/ml anti-$\alpha_v\beta_3$ integrin complex (LM609) or isotype-matched non-immune control antibody. This demonstrates integrin specificity of melanoma cell adhesion. Error bars indicate±standard deviation (n=3).

DETAILED DESCRIPTION OF THE INVENTION

Figure 3A:
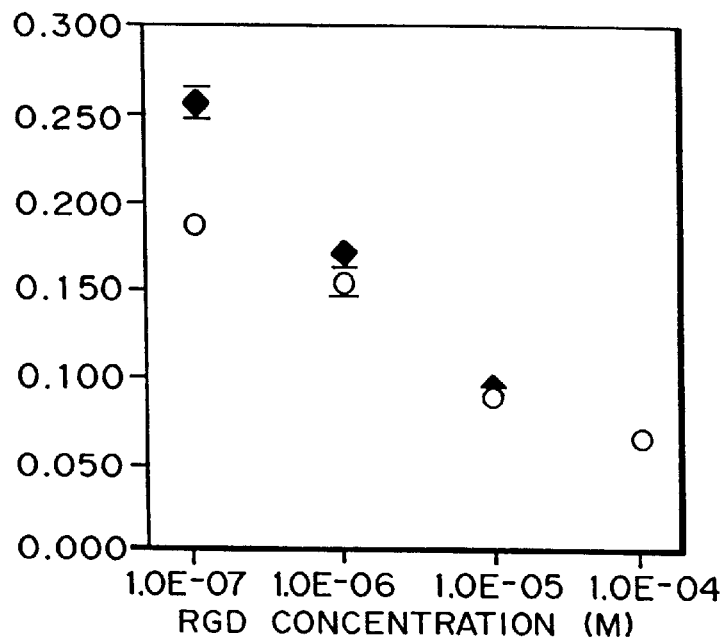
FIG. 3A is a graph of absorbance at 595 nm (representing adhered cells) versus concentration of RGD peptides used as a competitor of cell adherence to FN-SA (black diamonds) and OSTP-SA (white circles).

The disclosed compounds are modified forms of streptavidin that include a secondary functional domain. Streptavidin protein, which acts as a homotetramer, is a powerful biotin-binding protein. Because of this ability to bind biotin tightly, streptavidin is used as an adaptor in a wide variety of diagnostic, separations, and drug targeting applications, with the biotin/streptavidin interaction serving as the link. Many of these applications also require an effector molecule. As an adaptor, streptavidin often functions to immobilize a second protein (effector) such as a monoclonal antibody. This secondary protein then functions to capture a target, such as cells recognized by the antibody. The disclosed streptavidin molecules eliminate the need for associating such secondary proteins with streptavidin by incorporating the secondary function into the streptavidin molecule itself. Thus, the disclosed streptavidin molecules have been engineered to have an effector function that replaces the activity of the second protein.

It is thus advantageous that streptavidin itself can be used in some applications as both an adaptor and as an effector, which provides opportunities to simplify and improve many of these applications. Streptavidin has been engineered to include secondary functional domains by engineering functional peptide sequences into streptavidin, preferably in streptavidin three-dimensional scaffolding at defined surface locations.

A. Compounds and Compositions
1. Streptavidin

Wild type streptavidin is well known and has been described by, for example, Argarana et al., Nucleic Acids Research 14(4):1871–1881 (1986). The amino acid sequence of wild type streptavidin monomer is shown in SEQ ID NO: 1. The mature streptavidin protein begins at amino acid 25 in SEQ ID NO: 1. Wild type streptavidin can also be referred to as naturally occurring streptavidin. Modified forms of streptavidin having, for example, reduced binding affinity for biotin, can also be used in the disclosed molecules. Examples of such modified streptavidin are described in WO 96/24606. Streptavidin molecules having reduced binding affinity are useful, for example, since biotin and streptavidin can be separated using milder conditions than those needed with wild type streptavidin. Any form of streptavidin can be further modified to include a secondary functional domain as described herein and can be used for any purpose described herein for the disclosed modified streptavidin molecules or for any purpose for which the base form of streptavidin is used. The crystal structure of streptavidin is described by Weber et al., Science 243:85–88 (1989).

As used herein, unless otherwise indicated, streptavidin molecule refers to both streptavidin subunits (monomers) and multimeric streptavidin proteins such as the tetrameric streptavidin protein. Thus, for example, reference to a streptavidin molecule including a biotin binding domain and a secondary functional domain encompasses streptavidin monomers having a biotin binding domain and a secondary functional domain, streptavidin tetramers where each subunit has a biotin binding domain and a secondary functional domain, and mixed streptavidin tetramers where one, two, or three of the subunits have a secondary functional domain (and all the subunits have a biotin binding domain). As used herein, the modified streptavidin molecules containing a secondary functional domain disclosed herein can be referred to as, for example, mutant streptavidin, modified streptavidin, streptavidin derivatives, and streptavidin mutants. Unless otherwise indicated by the context, use of the terms mutant, derivative, and modified herein refer to modification to streptavidin that result in incorporation of a secondary functional domain into a base (starting) streptavidin molecule. It should be understood that the starting streptavidin can itself be a modified, derivative, or mutant form of streptavidin. As used herein, wild type streptavidin refers to any form of naturally occurring streptavidin.

2. Secondary Functional Domains

The disclosed streptavidin molecules are streptavidin molecules that have been modified to include one or more secondary functional domains. The secondary functional domain can be any molecule that has a useful function. It is preferred that the secondary functional domain is a sequence of amino acids. However, any form of molecule that can be coupled to streptavidin can be used as a secondary functional domain. Useful secondary functional domains include cell adhesion sequences, hormones, ligands for cell surface receptors, cell signaling molecules, cytokines, specific binding molecules, binding inhibitors, enzymes, specific binding molecules, and antigens.

A preferred secondary functional domain is the Arg-Gly-Asp (RGD) cell adhesive sequence. RGD is a well characterized peptide sequence responsible for integrin mediated cell adhesion that is found in fibronectin and many other extracellular matrix and matricellular proteins. Soluble RGD peptides are capable of inhibiting cell adhesion to a fibronectin coated surface, and RGD peptides mediate cell adhesion when immobilized on a surface. Pierschbacher, M. D. and Ruoslahti, E. (1984) Nature 309:30–33; Yamada, K. M. and Kennedy, D. W. (1984) J. Cell Biol. 99:29–36. Proteins without a native RGD domain have previously been genetically engineered to incorporate an RGD site that confers cell adhesive properties. Maeda, T. et al. (1989) J. Biol. Chem. 264:15165–15168; Hashino, K. et al. (1992) J.

Biochem. 112:547–551; Barbas III, C. F. et al. (1993) Proc. Natl. Acad. Sci. USA 90:10003–10007; Rossi, F. et al. (1995) Molec. Immunol. 32:341–346; Yamada, T. et al. (1995) J. Biol. Chem. 270:5687–5690; and Smith, J. S. et al. (1995) J. Biol. Chem. 270:30486–30490.

Two streptavidin mutants were prepared and characterized that incorporate the RGD sequence and flanking residues from fibronectin and osteopontin, referred to herein as FN-SA and OSTP-SA, respectively. These RGD streptavidin mutants are bifunctional proteins that retain wild type biotin affinity, yet also mediate cell adhesion in an RGD dependent manner. The RGD cell adhesive sequence has been used to exemplify the compositions and methods, but any number of peptide sequences providing secondary functions could be employed.

The secondary functional domain can be a specific binding molecule. Such a functional domain can thus provide the disclosed streptavidin molecules with a second specificity. A specific binding molecule is a molecule that interacts specifically with a particular molecule or moiety. Antibodies, either member of a receptor/ligand pair, and other molecules with specific binding affinities are examples of specific binding molecules, useful as the secondary functional domain of the disclosed streptavidin molecules.

A specific binding molecule that interacts specifically with a particular molecule or moiety is said to be specific for that molecule or moiety. For example, where the specific binding molecule is an antibody that binds to a particular antigen, the specific binding molecule is said to be specific for that antigen. Specific binding molecules are preferably antibodies, ligands, binding proteins, receptor proteins, haptens, or oligonucleotides.

3. Design of Molecules

The secondary functional domain can be incorporated into a streptavidin molecule in any suitable manner. It is preferred that the secondary functional domain be incorporated into the amino acid chain of streptavidin. In the case of functional domains that are peptides or proteins, this can be done, for example, by inserting the amino acid sequence of the secondary functional domain into the amino acid sequence of streptavidin, preferably at an exposed loop of streptavidin. A preferred exposed loop of streptavidin for incorporation of secondary functional domains is the loop at residues 63 to 69 of the streptavidin molecule between opposing β strands. This loop is on the opposite side of the biotin binding site of each monomer subunit.

For functional domains that are not peptides or proteins, the functional domain can be coupled to streptavidin (peptide and protein functional domains can also be coupled to streptavidin). Where coupling is used, the secondary functional domain can be directly coupled or coupled via a linker or spacer molecule.

RGD sequences are commonly found at the apex of a β-turn loop, like the type III β-turn for fibronectin. Main, A. L. et al. (1992) Cell 71:671–678. The anti-parallel β strands provide a constrained framework for the RGD loop. Cyclical peptides, which are comparable to loop structures, can demonstrate an enhanced activity over linear peptides of the same amino acid sequence. Pierschbacher, M. D. et al. (1987) J. Biol. Chem. 262:17294–17298.

An exposed loop of the streptavidin molecule between opposing β strands was thus chosen for the site of the RGD mutations (See FIG. 1). The chosen loop, residues 63 to 69, is on the opposite side of the biotin binding site of each monomer subunit, thus minimizing potential interference with biotin binding due to mutations or insertions of amino acids. The loop is also on the symmetry related surface which is maximally exposed to solution when streptavidin is bound to biotinylated surfaces. The initial design for introducing the RGD sequence into streptavidin substituted an Arg and Gly for residues Ala65 and Thr66, respectively, before a naturally occurring Asp67 residue. Two subsequently prepared mutants based on the original construct included additional flanking residues mimicking those found in fibronectin and osteopontin. A Gly was inserted between residues 64 and 65 (residues numbers correspond to mature wild type streptavidin), and a Ser and either a Val or a Pro (corresponding to fibronectin, FN-SA, and osteopontin, OSTP-SA, respectively) were placed between amino acids 67 and 68 (residues numbers correspond to mature wild type streptavidin). The sequences shown in Table I and SEQ ID NO:2 and SEQ ID NO:3 resulted. The amino acid sequences shown in Table 1 are amino acids 88 to 93 of SEQ ID NO:1 (wild type streptavidin), amino acids 88 to 95 of SEQ ID NO:2 (fibronectin streptavidin), and amino acids 88 to 95 of SEQ ID NO:3 (osteopontin streptavidin). These are amino acids 64 to 69 of mature wild type streptavidin, amino acids 64 to 71 of mature fibronectin streptavidin, and amino acids 64 to 71 of mature osteopontin streptavidin, respectively. SEQ ID NO:1 is the sequence of wild type streptavidin as reported by Argarana et al., Nucleic Acids Research 14(4):1871–1881 (1986).

TABLE 1

Comparison of the natural wild type streptavidin amino acid sequence to that of the two mutants with RGD segments inserted.

| Wild type Residue # | 64 | | 65 | 66 | 67 | | | 68 |
|---|---|---|---|---|---|---|---|---|
| Wild type Streptavidin | P | | A | T | D | | | G |
| Fibronectin Streptavidin | P | G | R | G | D | S | P | G |
| Osteopontin Streptavidin | P | G | R | G | D | S | V | G |

The additional flanking residues may increase the exposure of the loop and/or sterically optimize the adhesive sequences in a more favorable orientation. The flanking residues surrounding the RGD sequence also play a role in determining the adhesive activity of the peptide, as well as the specificity for individual integrins. This notion is supported by evidence with a series of synthetic peptides and inhibition studies indicating the presence of particular flanking residues is necessary for optimal binding activity. It has also been demonstrated through studies of cell spreading inhibition, that single alterations in the flanking amino acid residues of the RGD sequence can have significant effects on cell adhesion. Yamada, et al. (1984) The Journal of Cell Biology 99:29–36.

Nearly half of the known integrins display an RGD ligand binding dependence, and certain integrins require specific flanking sequences that differ amongst the various extracellular and matricellular proteins. D'Souza, S. E. et al. (1991) Trends in Biochem. Sci. 16:246–250. The different flanking residues are believed to alter the conformation of the RGD domain, thus providing a structural basis for integrin specificity. Previous reports have suggested that an RYD site inherent to wild type streptavidin can support cell binding, and that the native protein will compete with soluble RGD peptides for integrin engagement. Alon, R. et al. (1990) Biochem. Biophys. Res. Comm. 170:1236–1241; Alon, R. et al. (1992) Eur. J. Cell Bio. 58:271–279; Alon, R. et al. (1993) Eur. J. Immunol. 23:893–898. Such activity was not observed with the endothelial and melanoma cells used in the studies reported herein, or in other studies with a variety of cell types. The RYD sequence has limited solvent accessibility in the crystal structure of streptavidin, and is unlikely to be a strong mediator of specific integrin interactions with streptavidin.

In addition to specific flanking residues, the RGD sequence functions best when configured in a cyclical structure, such as in a naturally occurring flexible loop of a protein. This is especially true for loops situated between anti-parallel strands. Based on this criteria, such a loop, which appeared to have good exposure based on computer modeling of the streptavidin molecule, was chosen for the exemplified streptavidin mutants. As a result, the RGD streptavidin mutants retained a biotin affinity indistinguishable from that of wild type.

Multiple different functional domains can also be incorporated into streptavidin molecules. For example, a number of different peptide sequences with a variety of receptor specificities can be incorporated into an exposed loop or other surface locations, which could provide additional opportunities for cell separations and diagnostics applications. The incorporation of receptor specific peptide sequences allows use of the disclosed streptavidin molecules as both the targeting and capture agent in pre-targeting drug delivery applications utilizing biotinylated therapeutics.

4. Compounds For Use With Streptavidin Molecules

Any compound of interest can be targeted, delivered or immobilized using the disclosed streptavidin molecules. For example, the compound of interest can be a nucleic acid, protein, peptide, organic compound, inorganic compound, polysaccharide, or any combination of these. The compound of interest preferably has a therapeutic or bioactive effect. Examples of such compounds include antibiotics, antivirals, vaccines, vasodilators, antitumor agents, vasoconstrictors, immunomodulatory compounds, including steroids, antihistamines, and cytokines such as interleukins, colony stimulating factors, tumor necrosis factor and interferon (α, β, γ), oligonucleotides and nucleic acids including genes, nucleic acid vaccines, and antisense, nucleases, bronchodilators, hormones including reproductive hormones, calcitonin, insulin, erythropoietin, growth hormones, and bioactive organic compounds. Many other therapeutic and bioactive compounds are known and can be used with the disclosed streptavidin molecules.

Preferably, the compound of interest is biotinylated and thus interacts with (binds to) the biotin binding domain of the streptavidin molecule. Numerous techniques for biotinylating various molecules are known and can be used to produce biotinylated compounds. Alternatively, the compound of interest can be coupled to another compound or moiety that can interact with (bind to) the secondary functional domain of the streptavidin. The streptavidin molecule can also be designed so that the compound of interest itself can interact with the secondary functional domain.

The disclosed streptavidin molecules can also be immobilized, or used to immobilize other compounds, on substrates. Numerous support substrates are known and can be used with the disclosed streptavidin molecules. These include materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates for use with the disclosed streptavidin molecules can have any useful form including thin films or membranes, beads, bottles, dishes, fibers, woven fibers, shaped polymers, particles and microparticles. A preferred form for a solid-state substrate is a microtiter dish. The most preferred form of microtiter dish is the standard 96-well type.

B. Methods for Making Modified Streptavidin Molecules

The disclosed streptavidin mutants having a secondary functional domain may be made using methods known to those of skill in the art. These include chemical synthesis, modifications of existing proteins, and expression of proteins using recombinant DNA methodology.

The protein may be synthesized using standard chemical peptide synthesis techniques. Solid phase synthesis of peptides in which the C-terminal amino acid of the sequence is attached to an insoluble support followed by sequential additional of the remaining amino acids in the sequence is the preferred method for the chemical synthesis of the circularly permuted ligands and fusion proteins described herein. Techniques for solid phase synthesis are described by Barany and Merrifield, Solid-Phase Peptide Synthesis; pp. 3–284 in The Peptides; Analysis, Synthesis, Biology Vol. 2. Special Methods in Peptide Synthesis, Part A; Merrifield et al., *J. Am. Chem. Soc.* 85: 2149–2156 (1963); and Stewart et al., Solid Phase Peptide Synthesis, 2nd ed. Pierce Chem. Co., Rockford, Ill. (1984).

In preferred embodiments, the disclosed streptavidin proteins can be synthesized using recombinant methodology. Generally, this involves creating a polynucleotide sequence that encodes the protein, placing the polynucleotide in an expression cassette under the control of a suitable expression promoter, expressing the protein in a host, isolating the expressed protein and, if required, renaturing the protein.

DNA encoding a protein can be prepared by any suitable method. Many techniques for producing nucleic acid molecules of defined sequence are known, including restriction and ligation, site directed mutagenesis of a starting nucleic acid, PCR cloning techniques, and direct chemical synthesis. Such techniques can also be combined. It is preferred that nucleic acid encoding the starting streptavidin (for example, wild type streptavidin) be modified to produce nucleic acid encoding a streptavidin molecule containing a secondary functional domain.

Partial length sequences may be cloned and the appropriate partial length sequences cleaved using appropriate restriction enzymes. The fragments may then be ligated to produce the desired DNA sequence. In preferred embodiments, DNA encoding the polypeptide will be produced using DNA amplification methods, for example polymerase chain reaction (PCR).

Nucleic acid encoding the disclosed streptavidin molecules can also be made, in whole or in part, by chemical synthesis. Chemical synthesis produces a single stranded oligonucleotide. This may be converted into a double stranded DNA by hybridization with a complementary sequence, or by polymerization with a DNA polymerase using the single strand as a template. Those of skill recognize that while current methods for chemical synthesis of DNA are limited to preparing sequences of about 100 bases, longer sequences may be obtained by the ligation of shorter sequences. Useful methods of chemical synthesis include the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.*, 22: 1859–1862 (1981); and the solid support method of U.S. Pat. No. 4,458,066.

The encoded streptavidin molecules can be expressed in any suitable host cells, including *E. coli*, other bacterial hosts, yeast, and various higher eukaryotic cells, such as the COS, CHO and HeLa cells lines, insect cells, and myeloma cell lines. In preferred embodiments, the protein is encoded by a plasmid or a viral vector. The recombinant protein gene (that is, nucleic acid encoding the streptavidin molecule) is operable linked to appropriate expression control sequences for each host. For expression in *E. coli* the plasmid should include a promoter such as the T7, trp, or lambda promoters, a ribosome binding sight and preferably an enhancer, for example, derived from immunoglobulin genes, SV40, or cytomegalovirus, and a polyadenylation sequence, and may include spliced donor and acceptor sequences.

The plasmids encoding the fusion protein can be transferred into the chosen host cell by well known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes. Viral cells can be infected with vectors such as retroviral or adenoviral vectors.

Once expressed, the recombinant protein can be purified according to standard procedures of the art, including ammonium sulfate precipitation, affinity columns, column chromatography, gel electrophoresis and the like. Substantially pure compositions of at least about 90 to 95% homogeneity are preferred, and 98 to 99% or more homogeneity are most preferred for pharmaceutical uses. In particular, purification of the disclosed streptavidin molecules can be aided by affinity techniques involving either biotin or a ligand, binding partner, or specific binding molecule for the secondary functional domain. Once purified, partially or to homogeneity as desired, the streptavidin molecules may then be used as desired.

Those of skill in the art will recognize that after chemical synthesis, biological expression, or purification, the streptavidin molecules may possess a conformation substantially different than the native protein. In this case, it may be necessary to denature and reduce the streptavidin and then to cause the streptavidin to re-fold into the preferred conformation. Methods of reducing and denaturing proteins, including streptavidin, and inducing re-folding are well known to those of skill in the art. For example, the expressed, purified streptavidin may be denatured in urea or guanidium chloride and renatured by slow dialysis.

After purification, the streptavidin molecules can be assayed for biological activity as appropriate. For example, the streptavidin molecules can be assayed for biotin binding and/or the presence of the secondary function conferred by the secondary functional domain. Assays useful for this purpose are known to those of skill in the art and generally fall into two categories: those that measure the binding affinity of the streptavidin molecule to a particular target, and those that measure the biological activity of the streptavidin molecule.

C. Methods for Using Modified Streptavidin Molecules

The disclosed streptavidin derivatives having a secondary activity can be used for any purpose for which streptavidin can be used. This includes any procedure involving biotin/streptavidin binding. The disclosed streptavidin derivatives are particularly useful in techniques where it is desirable to associate a second molecule with streptavidin. Many such uses are known and all can be made more efficient by substituting the disclosed streptavidin derivatives for the separate streptavidin molecules and second molecules normally used.

The disclosed streptavidin molecules having a secondary functional domain can be used as a bridge or adaptor to target, deliver, immobilize, or join any compound, composition, structure, or object of interest to a second compound, composition, structure or object to which the streptavidin molecule can bind or become associated. The following examples illustrate these uses. For targeting to a cell, a streptavidin molecule containing a biotin binding domain and a cell adhesive sequence (the secondary functional domain) can be associated with a cell (via the cell adhesive sequence) and a biotinylated drug (the compound of interest) can be targeted or delivered to the cell through binding of the biotin moiety on the drug and the biotin binding domain on the streptavidin molecule. For immobilization, a streptavidin molecule containing a biotin binding domain and a specific binding molecule (the secondary functional domain)—for example, a ligand for a cell surface receptor—can be immobilized on a substrate via the biotin binding domain. Then a compound or composition (the compound of interest) that can bind to the specific binding molecule—for example, a cell—can then be immobilized on the substrate through binding of the compound to the specific binding molecule.

For diagnostic uses (that is, for detection of analytes), a streptavidin molecule containing a biotin binding domain and a specific binding molecule (the secondary functional domain) such as an antibody specific for an analyte can be immobilized on a biotinylated substrate (via the biotin binding domain) and the analyte (the compound of interest) can be immobilized on the substrate through binding of the analyte to the specific binding molecule on the streptavidin molecule. For affinity separation, a streptavidin molecule containing a biotin binding domain and a specific binding molecule (the secondary functional domain)—for example, an antibody specific for a compound of interest—can be immobilized on a substrate via the biotin binding domain. Then the compound of interest can be captured on the substrate through binding of the compound to the specific binding molecule. After washing the substrate, the compound can be eluted. Streptavidin molecules having reduced binding affinity are useful for affinity separation since biotin and streptavidin can be separated using milder conditions than those needed with wild type streptavidin (examples of such modified streptavidin are described in WO 96/24606). This allows the substrate to be cleared of streptavidin molecules with a minimum of damage to the substrate and streptavidin. In this way both the substrate and the streptavidin can be re-used. For example, the substrate can be loaded with a different form of streptavidin having a different secondary functional domain.

Many other combinations are possible with the bifunctional streptavidin serving as bridge between a biotinylated compound, structure or object, and a second compound that can interact with the secondary functional domain. As the examples above and elsewhere herein illustrate, the versatility of this bridging can be increased by coupling the second compound to yet another compound, structure or object.

A preferred use for the disclosed streptavidin derivatives are as coatings for substrates such as tissue culture dishes, vascular devices and prostheses. The secondary functional domain can then be used, for example, to immobilize cells, affect cell function, and/or serve as a scaffolding for cells. When the disclosed streptavidin derivatives are used as a coating for, or are immobilized on, a substrate, the secondary functional domain(s) can then recruit cells, alter or regulate cell function or activity, or immobilize specific molecules to the coated substrate.

Integrin mediated cell adhesion is closely tied to important signaling pathways that control cell behavior, and the disclosed streptavidin derivatives can also be used to stabilize cell phenotype through the incorporation of RGD or related sequences that mediate specific receptor mediated engagement and biology.

The present invention is further described by the following non-limiting examples.

EXAMPLES

Example 1

Preparation of DNA

Mutant forms of streptavidin were produced as follows. Oligonucleotides, 60 bases in length, were initially purchased from Integrated DNA Technologies (IDT) and shipped in lyophilized form. The FN-SA cassette was obtained by annealing the following complementary strands: 5'-CTAGGT ACGTTCTGACCGGTCGTTACGACTC-CGCTCCGGGTCGTGGTGACTCCC CGGGTT-3' (SEQ ID NO:4) and 5'-CCGGAACCCGGGGAGTCACCACGA CCCGGAGCGGAGTCGTAACGACCGGTCAGAACG TAC-3' (SEQ ID NO:5). The OSTP-SA cassette was constructed with the following strands: 5'-CTAGGTACGTTCTGACCGGTCGTTACGACTCCG CTCCGGGTCGTGGT GACTCCGTTGGTT-3' (SEQ ID NO:6) and 5'-CCGGAACCAACGGAGTC ACCACGAC-CCGGAGCGGAGTCGTAACGACCGGTC AGAACGTAC-3' (SEQ ID NO:7). The previously described streptavidin construct in pUC18, (Chilkoti A. et al. (1995) *Proc Natl Acad Sci USA* 92:1754–1758) was digested with restriction enzymes XbaI and BspEI (New England Biolabs) to create complementary ends for the annealed cassettes, which were subsequently ligated into the plasmid DNA. The ligation products were transferred into Nova-Blue competent cells (Novagen). The 60 mer fragment contained a single nucleotide mutation which eliminated the XbaI site from the streptavidin gene in order to screen for properly ligated candidates. Successful ligation was confirmed by fluorescent dye terminator cycle PCR sequencing. Upon confirmation of the sequencing, the mutated streptavidin gene was extracted from pUC 18 with an NdeI and HindIII (New England Biolabs) digest. Since the plasmid contained two NdeI sites, calculations were performed to determine the length of the fragment of interest. After the restriction digest, a second agarose gel was run to separate the linearized DNA and care was taken to excise the correct fragment. The DNA containing the streptavidin gene was then purified and ligated into the pET21a plasmid, previously digested with NdeI and HindIII, for subsequent subcloning. The plasmid was finally transformed into BL21 (DE3) (Novagen) competent cells in preparation for large scale streptavidin expression.

Example 2

Preparation of Streptavidin

The BL21(DE3) cells containing the pET21a plasmid with the streptavidin gene were used to inoculate an LB broth and allowed to grow-up overnight. The cells were then lysed to obtain the mutant streptavidin inclusion bodies and the inclusion bodies were washed until all of the cellular debris had been removed. During the lysing and washing process, the cells and inclusion bodies were sonicated in the appropriate buffer and then centrifuged to collect the inclusion bodies. The inclusion bodies were resolubilized in 6 M Guanidine/HCl overnight at 4° C. in a refrigerated cold room. Next the solubilized proteins were refolded (also at 4° C. overnight) and then the solution was centrifuged to remove aggregates and impurities prior to being concentrated with an Amicon filtration system under similar cold room conditions. After concentration, the protein was purified over an iminobiotin affinity chromatography column (Pierce), collecting the eluted volumes containing the streptavidin mutants. The collected volumes were recombined, placed back in the Amicon filtration system with TE saline, pH 7.0, and concentrated until the solution was equilibrated at a neutral pH level (about 7.0). Absorbance readings of diluted protein samples were taken to determine the final concentration and aliquots were stored at −20° C. for short periods of time and frequent use, whereas long-term storage was done at −80° C. to ensure greater stability of the protein.

Example 3

Protein Analysis

A. SDS-PAGE

A 10 to 20% Tris-Gly SDS-PAGE gel (Novex) was run with boiled and unboiled samples of the mutants, wild type streptavidin, and a Kaleidoscope molecular weight marker to analyze the structure and approximate molecular weight of the proteins. Unboiled samples reflect the tetramer streptavidin structure whereas the boiled samples dissociate into the monomer subunits. The wild type streptavidin was run as a control versus the two mutants to clearly visualize the molecular weight of the monomer and tetramer structures of streptavidin. In addition a native PAGE gel was performed by omitting SDS from the running buffer since the mutants appeared slightly unstable in the presence of SDS.

The SDS-PAGE gel indicated the monomer subunits of the mutant proteins were equal to the molecular weight of the wild type streptavidin monomer. The tetramer band for the unboiled wild type sample was clearly evident on the gel at a molecular weight of approximately 60,000. However, both of the mutants exhibited similar faint indications of the tetramer structure. The mutant tetramers ran slightly higher on the gel compared to wild type. Under native conditions unboiled samples of the mutant proteins again ran slightly higher on the gel, however the RGD mutants retained their tetramer structure in the absence of SDS.

The instability of the mutants' tetramer structures on the PAGE gel could be caused by the SDS running buffer introduced to the protein samples or the boiling of the sample. The RGD mutants will never be subjected to such harsh denaturing conditions, thus this demonstration of protein instability is not of concern for its intended purposes.

The slower migration of the streptavidin mutants on the PAGE gels compared to wild type should be expected due to the additional mass introduced from the extra residues inserted as well as the fact that the mutated arginine should add positive charge to the protein, which would slightly repel the proteins' attraction to the cathode during electrophoresis. An increase in the pI of the protein was calculated by the GCG program used to estimate the projected molecular weight of wild type streptavidin and the RGD mutants.

B. Mass Spectrometry

Mass spectrometry was performed on samples of the two streptavidin mutants by electron spray ionization mass spectrometry. The protein samples were prepared by dialyzing overnight versus distilled water and then boiled for 30 minutes in 25% methanol and 1% formic acid immediately prior to being run on the mass spectrometer.

Mass spectrometry provided accurate mass measurements for both of the streptavidin mutants within 1 to 2 mass units of their calculated molecular weights. The FN-SA sample was spiked with wild type streptavidin as a control. The wild type peak was visible at 13,268 and the FN-SA and OSTP-SA peaks were both observed at 13,554. The single residue differences between the two mutants, valine (OSTP-SA) and proline (FN-SA), are separated by only two mass units.

C. Kinetic Measurements

Since the mutations occur in a loop opposite from the biotin binding pocket, the rational design of the molecule should obviate any effect of reducing the off-rate, or dissociation constant of streptavidin. This indeed was observed by experimental $k_{off}$ values for the RGD mutants that are within the standard deviation of previously calculated values for wild type streptavidin. Off-rate measurements were performed at 25° C. to quantitatively characterize the biotin affinity of the mutants and compare the results of the binding affinity of wild type streptavidin. Tritiated biotin, "hot" because it is radioactively labeled, was added to samples of the mutant proteins in a PBS solution, pH 7.0, and allowed to equilibrate for 1 to 2 hours. The off-rate reaction was then initiated by the addition of 5 µL of 15 mM "cold" biotin (non-radioactive) in PBS. As the tritiated biotin dissociated from the streptavidin mutants, aliquots were taken at fixed times and scintillation counts were performed to analyze the beta emission of the tritiated biotin. The natural logarithm of the bound tritiated fractions was plotted versus time to attain the off-rate $k_{off}$, which is calculated from a linear regression of the data points.

Off-rate experiments indicated both mutants retained similar biotin affinity and dissociation rates as that of wild type streptavidin. At 25° C., the $k_{off}$ for wild type is $3.3\pm0.1\times10^{-6}$/sec compared to the $k_{off}$ of $3.28\times10^{-6}$/sec for FN-SA and $3.13\times10^{-6}$/sec for OSTP-SA.

The fact that protein elution was evident from the iminobiotin column was the first indication that the mutations in SA did not alter its function, namely its strong affinity to biotin. The off-rate experiments, in comparison to wild type streptavidin, clearly indicated the mutants retained normal biotin affinity and the quaternary protein structure was stable since streptavidin only binds to biotin in the tetramer configuration.

Example 4

Cell Adhesion

After the streptavidin mutants had been extensively characterized by a series of protein analysis techniques, a series of cell adhesion experiments were conducted to investigate whether the proteins exhibited cell binding via specific RGD-integrin engagement. Rat aortic endothelial cells were cultured in MDCB 131 media (Gibco BRL) with fetal bovine serum and used in the cell adhesion assays. Wild type and RGD streptavidin mutants were incubated in 96 well polystyrene plates overnight at 4° C. at various concentrations and then blocked with 1% BSA in PBS for 1 hour at 37° C. prior to the plating of cells (n=3). Alternatively, biotinylated BSA was incubated in the 96 wells overnight at 4° C., blocked with 1% BSA in PBS for one hour at 37° C., and then streptavidin (wild type or RGD) was incubated in the wells for one hour at 37° C. The protein solution was aspirated and the wells rinsed with sterile PBS before 50,000 cells were plated onto the protein coated wells for one hour at 37° C. The media was removed and the wells were rinsed twice with warm PBS (37° C.). The adherent cells were fixed with 4% paraformaldehyde (PFA) for 5 minutes and stained with 0.5% toluidine blue in 4% PFA for another 5 minutes at room temperature before the wells were rinsed by immersing the plate into a large bowl of tap water. The plate was dried by blotting the inverted plate onto paper towels and the remaining dye in the wells was solubilized with 1% SDS prior to reading the absorbance of the wells with a plate reader at 595 nm. The results are shown in FIGS. 2A and 2B.

Initial titration adhesion assays indicated a similar linear correlation for both RGD mutants between the amount of protein adsorbed and the proportion of adherent cells. Absorbance readings leveled off at approximately 0.30 for both mutants physiadsorbed to the polystyrene wells and both proteins adsorbed to wells coated with biotin-BSA. In both cases, saturation of cell adhesion was observed at a concentration of about 100 nM (5 µg/ml). Absorbance readings for wild type were comparable to those for 1% SDS, the solvent used to solubilize the toluidine for the readings.

Figure 3B:
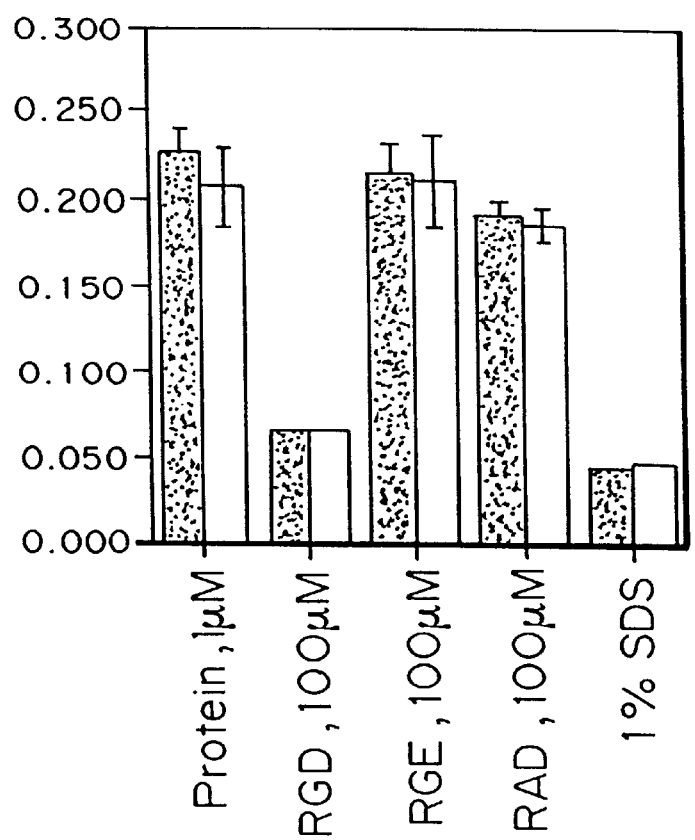
FIG. 3B is a bar graph of absorbance at 595 nm (representing adhered cells) using GRGDSP (amino acids 89 to 94 of SEQ ID NO:2), GRGESP (SEQ ID NO:8) and GRADSP (SEQ ID NO:9) soluble peptides as inhibitors of cell adherence to FN-SA (speckled bars) or OSTP-SA (white bars).

Wild type streptavidin does not display any cell adhesion above control levels. This was also confirmed by visually inspecting the wells with a phase-contrast microscope prior to introducing the fixative and cell stain (FIGS. 3A and 3B). A high number of cells remained adhered to the wells with the RGD streptavidin mutants, whereas very few cells remained in the wells coated with wild type streptavidin.

To confirm that the observed cell adhesion was directly RGD dependent, inhibition studies were conducted with GRGDSP (amino acids 89 to 94 of SEQ ID NO:2), GRGESP (SEQ ID NO:8), and GRADSP (SEQ ID NO:9) peptides. The results are shown in FIGS. 3A and 3B. The RGE and RAD control peptides had no noticeable inhibitory effect on cell adhesion, but the RGD peptide inhibited cell adhesion in a dose-dependent manner (FIG. 3A). 100 µm of the RGD peptide inhibited cell adhesion, while the two control peptides at the same concentration exhibited no appreciable inhibitory activity. This data confirms the cell adhesion activity of the streptavidin mutants is RGD mediated, as blocking of the integrin receptors with RGD peptides prior to plating inhibits cell adhesion.

The stark contrast in cell adhesion assays between the RGD mutants and wild type indicate the mutations were successful at performing their intended function. The low absorbance value for wild type reflects a background reading when compared to 1% SDS alone, thus it is safe to assume that practically no cells were capable of binding to streptavidin without the presence of the RGD mutation. This could also be confirmed by visualizing the wells during the adhesion assay prior to introducing the fixative and stain. A large number of cells remained adherent to the wells with the RGD streptavidins, whereas very few, if any cells remained in the wells coated with wild type.

Synthetic hexapeptides GRGDSP (amino acids 89 to 94 of SEQ ID NO:2), GRGESP (SEQ ID NO:8), and GRADSP (SEQ ID NO:9) were purchased from Gibco BRL. The inhibition assay was performed with the same protocol as for the cell adhesion assay except that the cells were incubated with the peptides for 15 minutes at room temperature prior to being plated onto the protein-coated wells.

Figure 4A:
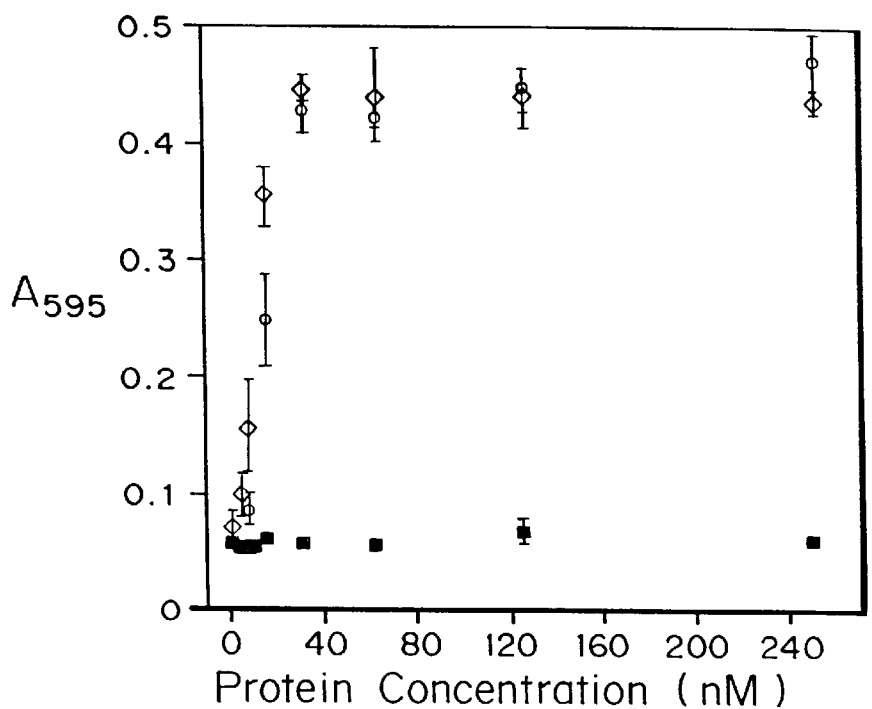
FIGS. 4A and 4B illustrate adhesion of melanoma cells to polystyrene dishes coated with FN-SA (diamonds), OSTP-SA (circles) and wild type streptavidin (black squares).
Figure 4B:
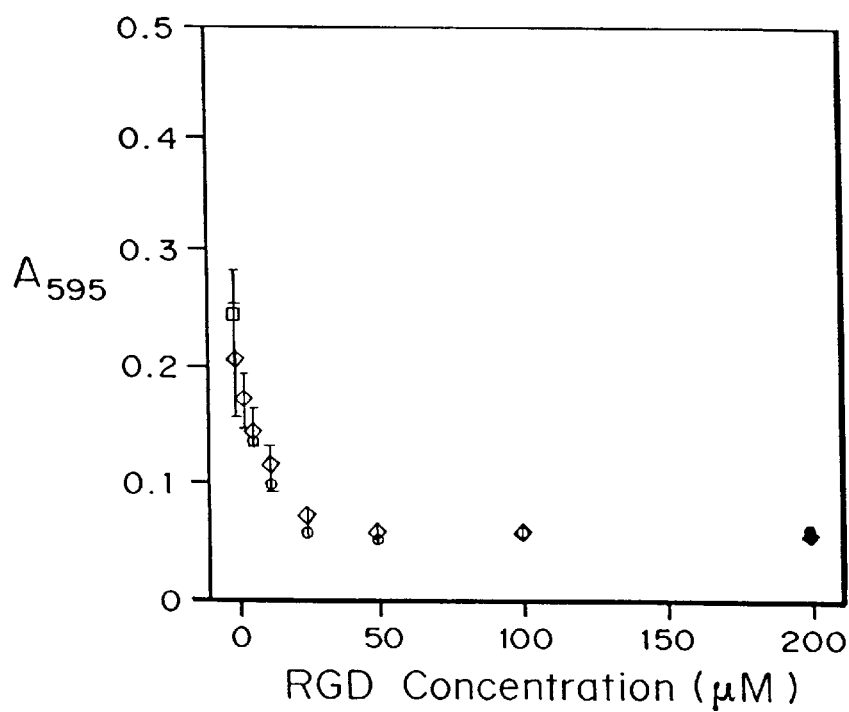
Figure 5A:
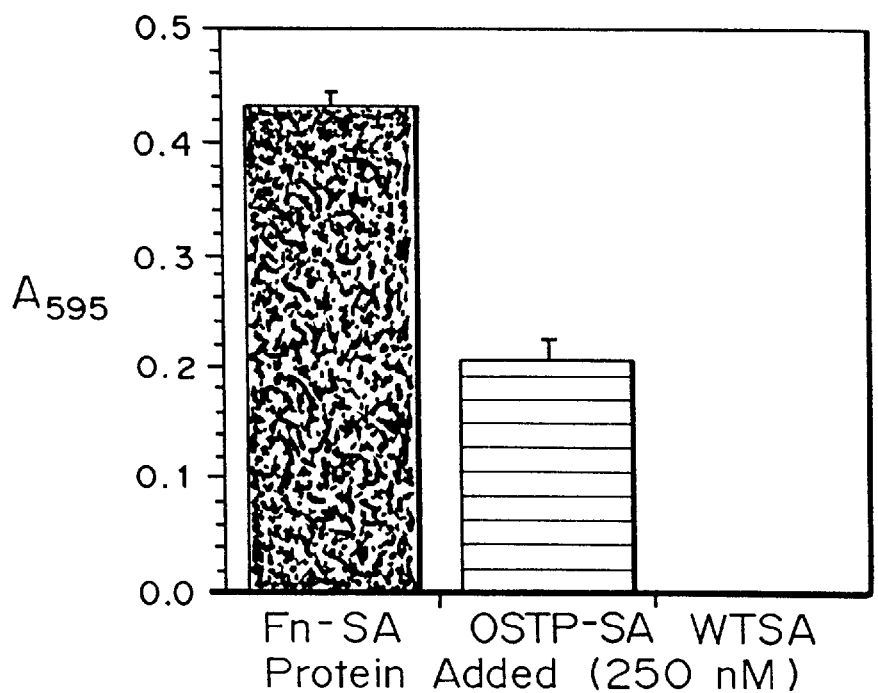
FIGS. 5A and 5B illustrate melanoma cell adhesion to mixed self assembled monolayers (SAMs) containing biotin and poly(ethylene glycol) thiols.
Figure 5B:
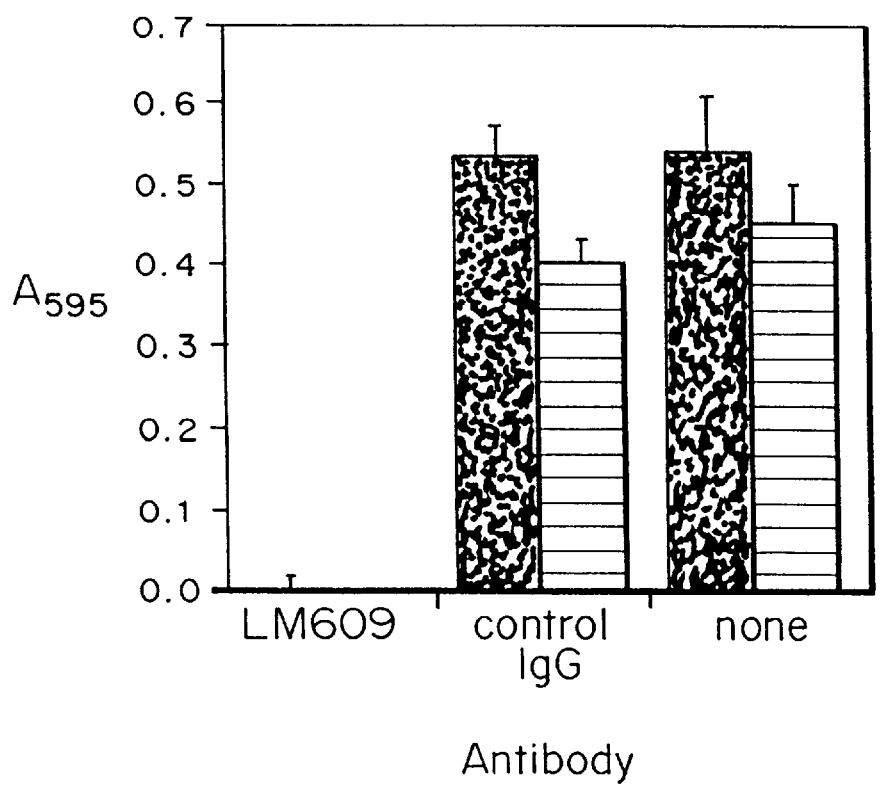

Melanoma cell adhesion assays on streptavidin coated polystyrene dishes were performed as described above for endothelial cell adhesion assays, except that DMEM with 0.1% BSA and 10 mM HEPES was used as culture medium and $2\times10^5$ cells were added to each well. $M\alpha_v$ cells that express high levels of $\alpha_v\beta_3$ integrin were derived from M21 melanoma cells. Adhesion assays were performed on self assembled monolayers constructed on 24 well tissue culture polystyrene dishes. The dishes were evaporated with about 400A gold, then incubated with a 0.1 mM ethanolic thiol solution of 20% biotinylated alkylthiol (BAT) and 80% polyethylene glycol (PEG) overnight. The wells were rinsed three times with 100% ethanol, blown dry with nitrogen, then incubated with 0.05 mg/ml of streptavidin in PBS (wild type or mutant) at 37° C. for one hour with side to side rocking. The protein solution was then removed, and the wells were rinsed three times with PBS before addition of cells. Antibody inhibition assays were performed essentially identically as for the RGD/RGE inhibition assays. LM609 and control were obtained from Chemicon International, Inc. (Calif.) and were used at 1:1000 dilution (10 μg/ml). Comparable cell adhesion results were obtained using human melanoma cells in addition to the endothelial cells. FIGS. 4A and 4B demonstrate that the RGD mutants show strong cell adhesive activity, and that this activity can be inhibited by the soluble RGD peptide. The cell adhesive activity can be inhibited by an anti-$\alpha_v\beta_3$ integrin monoclonal antibody, but not by a control nonspecific antibody (FIGS. 5A and 5B). These results thus demonstrate that the RGD sequence mediates cell adhesion, and that these sequences interact specifically with the $\alpha_v\beta_3$ integrin present on the melanoma cells.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a ", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A modified streptavidin monomer or multimeric molecule comprising a biotin binding domain and a secondary functional domain, wherein said secondary functional domain comprises the active domain of a heterologous polypeptide and wherein said secondary functional domain is inserted into the streptavidin molecule within an exposed loop of the streptavidin molecule.

2. The modified streptavidin molecule of claim 1, wherein said heterologous polypeptide is selected from the group consisting of cell adhesion sequences, hormones, ligands for cell surface receptors, cell signaling molecules, cytokines, specific binding molecules, binding inhibitors, enzymes, and antigens.

3. The modified streptavidin molecule of claim 1, wherein the secondary functional domain is incorporated into the streptavidin wild type polypeptide between amino acid residues 88 and 93 of SEQ. ID NO:1.

4. The modified streptavidin molecule of claim 3, wherein said molecule comprises amino acid residue substitutions Ala89Arg and Thr90Gly.

5. The modified streptavidin molecule of claim 1, wherein amino acid residues 89 to 91 of SEQ ID NO:1 have been replaced with Gly-Arg-Gly-Asp-Ser-Pro (amino acid residues 89–94 of SEQ ID NO:2).

6. The modified streptavidin molecule of claim 5, wherein said molecule comprises SEQ ID NO:2.

7. The modified streptavidin molecule of claim 1, wherein amino acid residues 89 to 91 of SEQ ID NO:1 have been replaced with Gly-Arg-Gly-Asp-Ser-Val (amino acid residues 89–94 of SEQ ID NO:3).

8. The modified streptavidin molecule of claim 7, wherein said molecule comprises SEQ ID NO:3.

9. The modified streptavidin molecule of claim 1, wherein said biotin binding domain has reduced biotin binding affinity.

10. A composition comprising the modified streptavidin of claim 1.

11. The composition of claim 10, wherein the modified streptavidin molecule is immobilized on a substrate selected from the group consisting of substrates for affinity separations, tissue culture dishes, and cell scaffolding.

12. The composition of claim 10, wherein the modified streptavidin molecule is immobilized on a substrate selected from the group consisting of a vascular devises or prosthesis.

* * * * *

SEQUENCE LISTING

```
<160> NUMBER OF SEQ ID NOS: 9

<210> SEQ ID NO 1
<211> LENGTH: 183
<212> TYPE: PRT
<213> ORGANISM: Streptomyces avidinii
<220> FEATURE:
<221> NAME/KEY: PEPTIDE
<222> LOCATION: (1)..(183)
<223> OTHER INFORMATION: Wild Type Streptavidin
<220> FEATURE:
<221> NAME/KEY: PROPEP
<222> LOCATION: (1)..(24)
<220> FEATURE:
<221> NAME/KEY: CHAIN
<222> LOCATION: (25)..(183)

<400> SEQUENCE: 1

Met Arg Lys Ile Val Val Ala Ala Ile Ala Val Ser Leu Thr Thr Val
 1               5                  10                  15

Ser Ile Thr Ala Ser Ala Ser Ala Asp Pro Ser Lys Asp Ser Lys Ala
                20                  25                  30

Gln Val Ser Ala Ala Glu Ala Gly Ile Thr Gly Thr Trp Tyr Asn Gln
            35                  40                  45

Leu Gly Ser Thr Phe Ile Val Thr Ala Gly Ala Asp Gly Ala Leu Thr
        50                  55                  60

Gly Thr Tyr Glu Ser Ala Val Gly Asn Ala Glu Ser Arg Tyr Val Leu
    65                  70                  75                  80

Thr Gly Arg Tyr Asp Ser Ala Pro Ala Thr Asp Gly Ser Gly Thr Ala
                85                  90                  95

Leu Gly Trp Thr Val Ala Trp Lys Asn Asn Tyr Arg Asn Ala His Ser
               100                 105                 110

Ala Thr Thr Trp Ser Gly Gln Tyr Val Gly Gly Ala Glu Ala Arg Ile
               115                 120                 125
```

```
Asn Thr Gln Trp Leu Leu Thr Ser Gly Thr Thr Glu Ala Asn Ala Trp
        130                 135                 140

Lys Ser Thr Leu Val Glu His Asp Thr Phe Thr Lys Val Lys Pro Ser
145                 150                 155                 160

Ala Ala Ser Ile Asp Ala Ala Lys Lys Ala Gly Val Asn Asn Gly Asn
                165                 170                 175

Pro Leu Asp Ala Val Gln Gln
            180
```

```
<210> SEQ ID NO 2
<211> LENGTH: 186
<212> TYPE: PRT
<213> ORGANISM: Artificial Sequence
<220> FEATURE:
<223> OTHER INFORMATION: Description of Artificial Sequence: FN-SA
<220> FEATURE:
<221> NAME/KEY: PROPEP
<222> LOCATION: (1)..(24)
<220> FEATURE:
<221> NAME/KEY: CHAIN
<222> LOCATION: (25)..(186)

<400> SEQUENCE: 2
```

```
Met Arg Lys Ile Val Val Ala Ile Ala Val Ser Leu Thr Thr Val
 1               5                  10                  15

Ser Ile Thr Ala Ser Ala Ser Ala Asp Pro Ser Lys Asp Ser Lys Ala
                20                  25                  30

Gln Val Ser Ala Ala Glu Ala Gly Ile Thr Gly Thr Trp Tyr Asn Gln
            35                  40                  45

Leu Gly Ser Thr Phe Ile Val Thr Ala Gly Ala Asp Gly Ala Leu Thr
    50                  55                  60

Gly Thr Tyr Glu Ser Ala Val Gly Asn Ala Glu Ser Arg Tyr Val Leu
65                  70                  75                  80

Thr Gly Arg Tyr Asp Ser Ala Pro Gly Arg Gly Asp Ser Pro Gly Ser
                85                  90                  95

Gly Thr Ala Leu Gly Trp Thr Val Ala Trp Lys Asn Asn Tyr Arg Asn
            100                 105                 110

Ala His Ser Ala Thr Thr Trp Ser Gly Gln Tyr Val Gly Gly Ala Glu
        115                 120                 125

Ala Arg Ile Asn Thr Gln Trp Leu Leu Thr Ser Gly Thr Thr Glu Ala
    130                 135                 140

Asn Ala Trp Lys Ser Thr Leu Val Glu His Asp Thr Phe Thr Lys Val
145                 150                 155                 160

Lys Pro Ser Ala Ala Ser Ile Asp Ala Ala Lys Lys Ala Gly Val Asn
                165                 170                 175

Asn Gly Asn Pro Leu Asp Ala Val Gln Gln
            180                 185
```

```
<210> SEQ ID NO 3
<211> LENGTH: 186
<212> TYPE: PRT
<213> ORGANISM: Artificial Sequence
<220> FEATURE:
<223> OTHER INFORMATION: Description of Artificial Sequence: OSTP-SA
<220> FEATURE:
<221> NAME/KEY: PROPEP
<222> LOCATION: (1)..(24)
<220> FEATURE:
<221> NAME/KEY: CHAIN
<222> LOCATION: (25)..(186)
```

<400> SEQUENCE: 3

Met Arg Lys Ile Val Val Ala Ala Ile Ala Val Ser Leu Thr Thr Val
 1               5                  10                  15

Ser Ile Thr Ala Ser Ala Ser Ala Asp Pro Ser Lys Asp Ser Lys Ala
                20                  25                  30

Gln Val Ser Ala Ala Glu Ala Gly Ile Thr Gly Thr Trp Tyr Asn Gln
            35                  40                  45

Leu Gly Ser Thr Phe Ile Val Thr Ala Gly Ala Asp Gly Ala Leu Thr
        50                  55                  60

Gly Thr Tyr Glu Ser Ala Val Gly Asn Ala Glu Ser Arg Tyr Val Leu
65                  70                  75                  80

Thr Gly Arg Tyr Asp Ser Ala Pro Gly Arg Gly Asp Ser Val Gly Ser
                85                  90                  95

Gly Thr Ala Leu Gly Trp Thr Val Ala Trp Lys Asn Asn Tyr Arg Asn
            100                 105                 110

Ala His Ser Ala Thr Thr Trp Ser Gly Gln Tyr Val Gly Gly Ala Glu
        115                 120                 125

Ala Arg Ile Asn Thr Gln Trp Leu Leu Thr Ser Gly Thr Thr Glu Ala
    130                 135                 140

Asn Ala Trp Lys Ser Thr Leu Val Glu His Asp Thr Phe Thr Lys Val
145                 150                 155                 160

Lys Pro Ser Ala Ala Ser Ile Asp Ala Ala Lys Lys Ala Gly Val Asn
                165                 170                 175

Asn Gly Asn Pro Leu Asp Ala Val Gln Gln
            180                 185

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
ctaggtacgt tctgaccggt cgttacgact ccgctccggg tcgtggtgac tccccgggtt     60

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
ccggaacccg gggagtcacc acgacccgga gcggagtcgt aacgaccggt cagaacgtac     60

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ctaggtacgt tctgaccggt cgttacgact ccgctccggg tcgtggtgac tccgttggtt     60

```
<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
ccggaaccaa cggagtcacc acgacccgga gcggagtcgt aacgaccggt cagaacgtac      60

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: peptide

<400> SEQUENCE: 8

Gly Arg Gly Glu Ser Pro
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: peptide

<400> SEQUENCE: 9

Gly Arg Ala Asp Ser Pro
 1               5
```